United States Patent [19]

Müller et al.

[11] 4,235,790

[45] Nov. 25, 1980

[54] PROCESS FOR SEPARATING P-BENZOQUINONE FROM THE REACTION PRODUCTS OF PHENOL OXIDATION AS QUINHYDRONE

[75] Inventors: Werner H. Müller, Eppstein; Dieter Freudenberger, Hofheim am Taunus, both of Fed. Rep. of Germany

[73] Assignee: Hoechst Aktiengesellschaft, Frankfurt am Main, Fed. Rep. of Germany

[21] Appl. No.: 5,570

[22] Filed: Jan. 22, 1979

[30] Foreign Application Priority Data

Jan. 24, 1978 [DE] Fed. Rep. of Germany ....... 2802863

[51] Int. Cl.$^3$ .................. C07C 46/10; C07C 50/04
[52] U.S. Cl. .................. 260/396 R; 568/772
[58] Field of Search .................. 260/396 R

[56] References Cited

U.S. PATENT DOCUMENTS

| | | | |
|---|---|---|---|
| 1,987,148 | 1/1935 | Kleimenhagen | 260/396 R |
| 2,281,327 | 4/1942 | Schumacher et al. | 260/396 R |

*Primary Examiner*—Vivian Garner
*Attorney, Agent, or Firm*—Curtis, Morris & Safford

[57] ABSTRACT

A process for separating p-benzoquinone as quinhydrone from the reaction solution obtained in the oxidation of phenol with oxygen in the presence of copper salts and of nitriles as the solvent, which comprises suspending and/or dissolving solid hydroquinone in this reaction solution, precipitating the p-benzoquinone contained therein as quinhydrone and separating it from the reaction solution.

5 Claims, No Drawings

PROCESS FOR SEPARATING P-BENZOQUINONE FROM THE REACTION PRODUCTS OF PHENOL OXIDATION AS QUINHYDRONE

The present invention relates to a process for separating p-benzoquinone as quinhydrone from the reaction products obtained in the phenol oxidation with oxygen in the presence of copper salts. In this process p-benzoquinone is separated in the form of its addition compound with hydroquinone, namely quinhydrone. Quinhydrone can be readily converted into quinone or hydroquinone. Aqueous $NaClO_3$, for example may be used in the oxidation giving quinone. Quinhydrone may be reduced to hydroquinone by catalytic hydrogenation. Hydroquinone is used as a photographic developer, as an antioxidant and as a polymerization inhibitor.

It is known to obtain p-benzoquinone by catalytic oxidation of phenol. In this process solutions of phenol are oxidized by oxygen to p-benzoquinone in the presence of copper halide catalysts with the use of nitriles, for example acetonitrile, as the solvent.

A typical feature of these known oxidation processes is that they result in complex and in most cases heterogeneous reaction mixtures. In order to obtain a pure p-benzoquinone that is easy to hydrogenate, these mixtures must be worked up, which is extremely difficult and requires complicated and uneconomic distillation or extraction separation methods involving high losses.

A great disadvantage in the subsequent hydrogenation of the p-benzoquinone obtained resides in the fact that the copper halides used as catalysts in the phenol oxidation partially lose their halogen constituents, which are then incorporated in by-products, which are very difficult to separate from p-benzoquinone. As a consequence, the catalysts used in the subsequent p-benzoquinone hydrogenation suffer from a rapid loss of activity, since they become contaminated by halogen. The further processing is moreover rendered difficult by the copper halides themselves.

The problem was therefore the development of a simple, technically acceptable method for separating p-benzoquinone, in which unconverted phenol, if any, or catalyst material, for example $CuCl_2$ or chlorine evolved therefrom, do not unfavorably affect a subsequent hydrogenation of the quinone.

It is known that quinone reacts with hydroquinone to give quinhydrone, which is relatively insoluble. It is also known to separate quinone in the form of quinhydrone from benzene solutions formed in electrochemical benzene oxidation processes by precipitation with aqueous hydroquinone solutions.

This separation method cannot be employed without a detrimental effect on the p-benzoquinone obtained in phenol oxidation processes, since acetonitrile preferably used as the solvent is miscible with aqueous hydroquinone solutions in any ratio, which would result in an undesired and progressively difficult reversible dilution of the mother liquors to be recycled to the phenol oxidation process. Furthermore, the yields of benzoquinone decrease with an increasing water content of the acetonitrile in the oxidation of the unsubstituted phenol.

A simple and very economic process for separating p-benzoquinone from the reaction solutions formed in a phenol oxidation process of the above type using oxygen and copper salts has now been found which solves the problems encountered previously in the further processing of p-benzoquinone in a surprisingly simple manner by precipitating the p-benzoquinone present in these solutions in the form of a pure quinhydrone that is completely halogen free and can be subsequently hydrogenated without difficulty in known manner by adding solid hydroquinone. Half of the quantity of hydroquinone present upon the quinhydrone hydrogenation is recycled and reused for a further quinone precipitation. A removal of solvent is not required. The mother liquors remaining upon the quinhydrone separation can be recycled without difficulty to the phenol oxidation process.

The present invention, consequently, relates to a process for separating p-benzoquinone from the reaction solution obtained in the oxidation of phenol with oxygen in the presence of a copper salt and a nitrile as solvent, which comprises suspending and/or dissolving solid hydroquinone in said reaction solution, precipitating the p-benzoquinone contained therein as quinhydrone and separating it from the reaction solution.

In this separation process, the solid hydroquinone is simply stirred into the copper halide-containing acetonitrile solution of p-benzoquinone contaminated by phenol, for example. It is surprising that catalyst material such as copper ions or copper halides neither precipitates in complex form nor is otherwise incorporated into the quinhydrone. Furthermore, unconverted phenol of the oxidation process does not precipitate in the form of phenoquinone although it is known that this substance tends to form crystals easily.

Hence, the instant process yields a very pure quinhydrone, which can be converted immediately, for example by catalytic hydrogenation, into hydroquinone that is likewise very pure, without involving a loss of hydrogenation activity, for example of the Ni or Pd catalysts, in continuous operation.

The separation process according to the invention is suitably carried out in the following manner: First the p-benzoquinone content of a reaction solution resulting from a known phenol oxidation is determined. For this purpose the classical analytical methods of titration with potassium iodide and thiosulfate and gas chromatographic determination may be employed.

This makes it possible to add the stoichiometrically required quantity of hydroquinone without any excess which would remain in solution. On the other hand all p-benzoquinone is reacted and separated as quinhydrone. Hence, it is generally advisable for economic reasons to add stoichiometric quantities of hydroquinone. However, even when not working with stoichiometric quantities, the quinone may be separated as quinhydrone.

It is generally advisable to start with concentrated solutions of p-benzoquinone of at least 0.5% of p-benzoquinone and at least 2%, being particularly preferred. Since the reaction solutions generally obtained in known phenol oxidations using for example $CuCl_2 \cdot 2H_2O$ in acetonitrile contain more than 5% of p-benzoquinone, further measures can be dispensed with. However, it is similarly possible to attain the preferred minimum concentration by partially removing the solvent, for example by thin layer distillation so that relatively small residual quantities of p-benzoquinone can be precipitated. In general from about 98 to 99% of the p-benzoquinone formed is precipitated in the form of very pure quinhydrone without further procedures.

The p-benzoquinone is generally separated at a temperature from 0° to 150° C., preferably from 0° to 100°

C. and particularly from 20° to 50° C. in either discontinuous or continuous manner. When oxidizing phenol, for example, at a temperature of 40° C., hydroquinone can be added directly in solid form upon filtration of the reaction solution, without further measures such as cooling or heating. It can be observed in this process that the quinhydrone begins to precipitate while the hydroquinone is still dissolving. The precipitation may be carried out under a slightly elevated pressure or under reduced pressure. In general a pressure from 0.5 to 5.0 bars is applied.

The quinhydrone obtained according to this novel and extremely simple method has a purity of more than 99% without being subjected to a further treatment. Surprisingly it does not contain phenol or any inorganic or organic chlorine-containing components such as included $CuCl_2$ or $CuCl_2$ bound in complex manner.

The remaining mother liquors that may contain phenol and dissolved copper compounds may be reused in the phenol oxidation without difficulty. Insignificant quantities of quinone, hydroquinone or quinhydrone possibly remaining in the mother liquor do not hinder the phenol oxidation. They are separated in the following precipitation operation along with the freshly formed p-benzoquinone.

The quinhydrone that has been precipitated and separated in the usual manner as for example by centrifugation or filtration, can be converted into hydroquinone in known manner. For this purpose the quinhydrone is hydrogenated, for example in ethers such as tetrahydrofuran, dioxan or dimethylglycol or in water or alcohols in the presence of a nickel or palladium catalyst at a temperature of from 40° to 100° C. under a pressure of from 1 to 100 bars. The catalysts may be reused several times without suffering a loss of activity.

The following method has proved particularly advantageous: Solid hydroquinone is stirred into the solution of p-benzoquinone in acetonitrile prepared in usual manner, optionally, while slightly heating and after some time the precipitated quinhydrone is separated by filtration or centrifugation.

The following examples illustrate the invention.

EXAMPLE 1

10 g of phenol (0.106 mol) are dissolved in 200 ml (156 g) of acetonitrile and the resulting solution is poured into a 1 liter autoclave with shaking device along with 2.8 g of $CuCl \cdot 2H_2O$. Then oxygen is added until the pressure amounts to 70 bars and the reaction batch is heated rapidly to 52° to 54° C. After one hour the reaction is stopped. The contents are then cooled to room temperature (about 20° C.) and the reaction mixture (170 g) is analyzed.

The reaction mixture contains 5.63% by weight of quinone (9.57 g=0.088 mol). 9.75 g (0.088 mol) of solid, analytically pure hydroquinone are added to this mixture, which is then stirred at room temperature whereby the hydroquinone is dissolved. After briefly stirring, the quinhydrone begins to precipitate. Precipitation is terminated after about 30 minutes. By filtration 17.65 g of quinhydrone are obtained. A further 0.98 g of quinhydrone is precipitated in a second step by cooling or careful concentration of the solution, which corresponds to a yield of 96.4% (calculated on the analytically determined p-benzoquinone content of the reaction solution obtained in the phenol oxidation) of practically analytically pure quinhydrone.

The filtrate can be reused in the phenol oxidation.

The quinhydrone is dissolved in dimethylglycol and hydrogenated to hydroquinone with hydrogen in the presence of a $Pd/SiO_2$ catalyst at 40° C. under 40 bars (yield 99.8%). A part of the pure hydroquinone thus obtained is reused for the precipitation of the p-benzoquinone as quinhydrone.

EXAMPLE 2

20 g of phenol (0.212 mol) are dissolved in 100 ml of acetonitrile (78 g) and 1.4 g of $CuCl_2$ (anhydrous) are added. The mixture is placed in a magnetic type lifting, stirring autoclave and heated to 53° C. Then oxygen is added until a pressure of 65 bars is reached. The mixture is allowed to react at this temperature for 1.5 hours while stirring.

Then the mixture is cooled and the reaction solution is filtered off and analyzed.

97.9 g of filtrate are obtained containing 17.7 weight % of p-benzoquinone (17.32 g=0.16 mol).

17.61 g (0.16 mol) of crystallized hydroquinone are added to this filtrate while stirring. While the hydroquinone begins to dissolve, the quinhydrone begins to precipitate. Stirring is continued for about 45 minutes while slightly heating to 30° to 40° C. and then the crystalline mass is filtered off.

32.8 g of quinhydrone (0.15 mol=94%, calculated on p-benzoquinone) are obtained as practically analytically pure product (purity 99.83%).

By cooling of the mother liquor a further 1.2 g of quinhydrone is obtained.

EXAMPLE 3

10 g of phenol (0.106 mol) are dissolved in 100 ml of acetonitrile (78 g), 1.4 g CuCl are added and the mixture is introduced into a 0.5 liter magnetic type lifting stirring autoclave. Oxygen is then added until a pressure of 55 bars is reached and the mixture is heated to 50° C.

After 45 minutes, the reaction is discontinued and after cooling to 20° C., the reaction mixture is filtered and analyzed.

87.2 g of reaction solution are obtained containing 10.9 weight % of p-benzoquinone (9.50 g=0.088 mol).

The test is repeated twice and the reaction solutions which contain 9.38 g of p-benzoquinone after the second test and 9.56 g of p-benzoquinone after the third test are combined.

To this mixture combined from three batches (altogether 261 g) and containing 28.4 g of p-benzoquinone (0.262 mol), 28.9 g of hydroquinone (0.262 mol) are added. The mixture is slightly heated to 40° C., stirred for 2 hours, cooled in an ice bath and the crystalline mass is suction-filtered from the mother liquor. 53.1 g of quinhydrone (92.6% of the theory) having a purity of 99.8% according to gas chromatographic analysis are obtained.

By carefully concentrating the mother liquor in a rotation evaporator and again cooling to 2° to 5° C. a small residual quantity of quinhydrone (3.5 g, purity 96.1%) is recovered.

EXAMPLE 4

20 g of phenol (0.212 mol) are dissolved in 100 ml (78 g) of acetonitrile. Then 1.4 g of anhydrous CuCl (0.014 mol) as catalyst are added. The mixture is placed in a 0.5 liter autoclave. Oxygen is added until a pressure of 40 bars is reached and the mixture is heated for 1 hour to 40° C. Then the reaction is discontinued. 98 g of a dark red-brown solution containing 9.1 weight % of phenol (8.9 g=0.094 mol) and 9.6 weight % of p-benzoquinone (9.41 g=0.087 mol) are obtained.

9.57 g (0.087 mol) of solid hydroquinone are added to this solution. The mixture is heated to 50° C. and allowed to cool to room temperature in 1.5 hours while stirring. Then the mixture is cooled to 0° C. in an ice bath, the precipitated quinhydrone is suction-filtered and washed with 20 ml of cold acetonitrile. 17.78 g of quinhydrone (94.1% of the theory) are obtained containing no phenol or phenoquinone according to gas chromatographic analysis.

COMPARATIVE EXAMPLE 1

(Direct hydrogenation of the quinone without previous precipitation as quinhydrone)

10 g of phenol (0.106 mol) are dissolved in 200 ml of acetonitrile (156 g), then 2.8 g of $CuCl_2 \cdot 2H_2O$ are added and the mixture is placed in a 1 liter autoclave with shaking device. Oxygen is added until a pressure of 70 bars is reached and the mixture is heated rapidly to 52° to 55° C. After 1 hour the reaction is discontinued and 165 g of reaction solution containing 5.3 weight % (8.7 g=0.081 mol) of p-benzoquinone are obtained.

Without separation of the quinone as quinhydrone the solution is placed in an autoclave and submitted to hydrogenation for 2 hours in the presence of a $Pd-SiO_2$ catalyst. 161 g of a reaction solution are obtained in which only 0.8 weight % of hydroquinone (1.29 g=0.012 mol, which corresponds to 14.4% of the theory) is obtained. The superiority of the process of the invention with precipitation of the quinone as quinhydrone and subsequent hydrogenation is obvious.

COMPARATIVE EXAMPLE 2

(Use of an aqueous hydroquinone solution)

10 g of phenol (0.106 mol) are dissolved in 200 ml of acetonitrile. Then 25 ml of water and 2.8 g of $CuCl_2 \cdot 2H_2O$ are added and the mixture is placed in a 1 liter autoclave with shaking device. Then oxygen is added until a pressure of 70 bars is reached and the mixture is heated rapidly to 55° C. After one hour the reaction is discontinued. 188 g of a reaction solution are obtained containing 4.1 g of quinone (0.038 mol, which corresponds to 35.9% of the theory).

To this solution 4.17 g of hydroquinone (0.038 mol) in 25 ml of water are added and the mixture is cooled to 0° C. in an ice bath for 2 hours. Then the precipitated quinhydrone (6.7 g=81% of the theory) is filtered off and hydrogenated in usual manner.

The reaction solution freed from p-benzoquinone is reused in the phenol oxidation, after having added 10 g of phenol and 2.8 g of $CuCl_2 \cdot 2H_2O$ as in the first passage. After 8 repetitions of the phenol oxidation and the quinhydrone precipitation there is obtained by progressive dilution with water (effected by the quinhydrone precipitation by means of aqueous hydroquinone solution) a solution containing about 1 part of acetonitrile per 1 part of water. The phenol oxidation is again carried out in this medium. Then only 1.14 g of quinone are obtained from 10 g of phenol (a yield of about 10%).

What is claimed is:

1. A process for separating p-benzoquinone as quinhydrone from a reaction solution obtained in the oxidation of phenol with oxygen in the presence of a copper salt and a nitrile as solvent, which comprises suspending and/or dissolving solid hydroquinone in said reaction solution, precipitating the p-benzoquinone contained in the reaction solution as quinhydrone and separating the quinhydrone from the reaction solution.

2. The process of claim 1, which comprises separating the p-benzoquinone as quinhydrone at a temperature from 0° to 100° C.

3. The process of claim 1, which comprises separating the p-benzoquinone as quinhydrone under a pressure from 0.5 to 5 bars.

4. The process of claim 1 wherein the p-benzoquinone is present in the reaction solution in a concentration of at least 2 percent by weight.

5. The process of claim 1 wherein at least 98 to 99 percent by weight of the p-benzoquinone present in the reaction solution is precipitated as quinhydrone.

* * * * *